US007893025B2

(12) United States Patent
Lussier et al.

(10) Patent No.: US 7,893,025 B2
(45) Date of Patent: Feb. 22, 2011

(54) USE OF GROWTH HORMONE RELEASING FACTOR ANALOGS IN TREATING PATIENTS SUFFERING FROM WASTING

(75) Inventors: Bruno Lussier, Saint-Lambert (CA); Luc Vachon, Montreal (CA); Soraya Allas, Outremont (CA); Thierry Abribat, St-Foy-Les-Lyon (FR)

(73) Assignee: Theratechnolgies Inc., Saint-Laurent, Quebec (CA)

( * ) Notice: Subject to any disclaimer, the term of this patent is extended or adjusted under 35 U.S.C. 154(b) by 1009 days.

(21) Appl. No.: 10/576,439

(22) PCT Filed: Oct. 20, 2004

(86) PCT No.: PCT/CA2004/001843

§ 371 (c)(1),
(2), (4) Date: Jan. 5, 2007

(87) PCT Pub. No.: WO2005/037307

PCT Pub. Date: Apr. 28, 2005

(65) Prior Publication Data

US 2008/0167222 A1    Jul. 10, 2008

Related U.S. Application Data

(60) Provisional application No. 60/512,198, filed on Oct. 20, 2003.

(51) Int. Cl.
*A61K 38/25*    (2006.01)
(52) U.S. Cl. .................................................. 514/11.2
(58) Field of Classification Search ........................ None
See application file for complete search history.

(56) References Cited

U.S. PATENT DOCUMENTS

| 6,423,693 | B1 * | 7/2002  | Schwartz et al. | 514/44 R |
| 6,458,764 | B1 * | 10/2002 | Gravel et al.   | 514/12   |
| 7,316,997 | B2 * | 1/2008  | Abribat et al.  | 514/2    |
| 2009/0011985 | A1 * | 1/2009 | Abribat et al. | 514/12   |
| 2009/0088383 | A1 * | 4/2009 | Abribat et al. | 514/12   |
| 2009/0253623 | A1 * | 10/2009 | Abribat et al. | 514/12   |

FOREIGN PATENT DOCUMENTS

| CA | 2 367 461     | 9/2000  |
| CA | 2 357 853     | 3/2002  |
| WO | WO 2004/105789 A1 | 12/2004 |

OTHER PUBLICATIONS

Larocque et al. "Anchoring rigid hydrophobic chains to stabilize growth hormone-releasing factor," APS Poster, 2001).*
Debigare et al. "Peripheral Muscle Wasting in Chronic Obstructive Pulmonary Disease," Am. J. Respir. Crit. Care Med., vol. 164, No. 9, Nov. 2001, 1712-1717.*
Burdet et al. "Administration of Growth Hormone to Underweight Patients with Chronic Obstructive Pulmonary Disease." *Am J. Respir Crit Care Med.* vol. 156. 1997. pp. 1800-1806.
Ferreira et al. "The Influence of 6 Months of Oral Anabolic Steroids on Body Mass and Respiratory Muscles in Undernourished COPD Patients." *Chest* vol. 114, No. 1. Jul. 1998. pp. 19-28.
Ferreira et al. Nutritional Support for Individuals with COPD. *Chest* vol. 117. No. 3. Mar. 2000. pp. 672-678.
Morabia et al. "Relation of BMI to dual-energy X-ray absorptiometry measure of fatness." *British Journal of Nutrition.* vol. 82. 1999. pp. 49-55.
Pape et al. "The Effect of Growth Hormone on Weight Gain and Pulmonary Function in Patients with Chronic Obstructive Lung Disease." *Chest* vol. 99, No. 6. Jun. 1991. pp. 1495-1500.
Schambelan et al. "Recombinant Human Growth Hormone in Patients with HIV-Associated Wasting." *Annals of Internal Medicine* vol. 125, No. 11. 1996. pp. 873-882.
Schols et al. "Weight Loss Is a Reversible Factor in the Prognosis of Chronic Obstructive Pulmonary Disease." *Am J Respir Crit Care Med.* vol. 157. 1998. pp. 1791-1797.
Weisberg et al. "Megestrol Acetate Stimulates Weight Gain Ventilation in Underweight COPD Patients." *Chest.* vol. 121, No. 4. Apr. 2002. pp. 1070-1078.
Zachwieja et al. "Does Growth Hormone Therapy in Conjunction with Reistance Exercise Increase Muscle Force Production and Muscel Mass in Men and Women Aged 60 Years or Older." *Physical Therapy.* vol. 79, No. 1. Jan. 1999, pp. 76-82.
Written Opinion mailed Mar. 2, 2005 from PCT Appln. No. PCT/CA2004/001843.
Lieber, R.L. et al., "Growth Hormone Secretagogue Increases Muscle Strength during Remobilization after Canine Hindlimb Immobilization", Journal of Orthopaedic Research, 1997, vol. 15, pp. 519-527.
Theratechnologies Inc., "Theratechnologies and Sakai Chemical sign landmark licensing agreement to develop and market ThGRF peptide in Japan", online, Feb. 5, 2002.
Theratechnologies Inc., "Theratechnologies annonces positive results of an efficacy and safety phase II clinical trial of ThGRF in sleep maintenance insomnia", online, May 29, 2002.
Theratechnologies Inc., "Theratechnologies clinically demonstrates improvement in immune function among elderly with ThGRF peptide", online, Jun. 6, 2002.
Theratechnologies Inc., "Theratechnologies: phase II clinical study completed in the United States", online, Nov. 22, 2002.
Theratechnologies Inc., "Theratechnologies: US phase II clinical study confirms safety of ThGRF in patients with Type II diabetes", online, Jan. 29, 2003.

(Continued)

*Primary Examiner*—Christina Bradley
(74) *Attorney, Agent, or Firm*—Merchant & Gould P.C.

(57) ABSTRACT

The present invention provides methods for using growth hormone releasing factor analogs of the formula (A), X-GRF Peptide, and pharmaceutically acceptable salts thereof, for increasing muscle function in a subject. Also disclosed herein are corresponding methods, packages and compositions.

12 Claims, 5 Drawing Sheets

OTHER PUBLICATIONS

Theratechnologies Inc., "Theratechnologies: financial results for the first quarter of 2003", online, Apr. 17, 2003.

Theratechnologies Inc., "Theratechnologies completes patients enrolment for its clinical study on chronic obstructive pulmonary disease as part of its phase II program on ThGRF", online, Apr. 23, 2003.

Theratechnologies Inc., "Theratechnologies initiates phase II clinical trial in Canada and the US for ThGRF in HIV-related lipodystrophy", online, May 22, 2003.

Theratechnologies Inc., "Theratechnologies presents data on its development programs at the 85th annual meeting of the endocrine society", online, Jun. 10, 2003.

Theratechnologies Inc., "Theratechnologies presents data on its development programs at the 85th annual meeting of the endocrine society", online, Jun. 20, 2003.

Theratechnologies Inc., "Theratechnologies: patient enrolment completed in hip fracture phase II clinical for ThGRF", online, Jul. 9, 2003.

Theratechnologies Inc., "Theratechnologies: financial results for the second quarter of 2003", online, Jul. 14, 2003.

Theratechnologies Inc., "Theratechnologies: financial results for the third quarter of 2003 and recent operating highlights", online, Apr. 17, 2003.

Pichard et al., "Recombinant Human Growth Hormone in Chronic and Acute Respiratory Insufficiency", *Hormone Research*, 1996, 46:222-229.

Lissett et al., "Effects of growth hormone on bone and muscle", *Growth Hormone & IGF Research*, 2000, Supplement B, S95-S101.

Maltais et al., "Effects of TH9507, A growth-hormone-releasing factor (GRF) analogue, on functional performance in patients with COPD." <http://www.theratech.com/docs/en/scientifiques/74/ers2.pdf> retrieved on Mar. 18, 2010. XP002574024.

Supplementary European Search Report for corresponding EP application EP 04 78 9750, mailed on Mar. 19, 2010.

* cited by examiner

USE OF GROWTH HORMONE RELEASING FACTOR ANALOGS IN TREATING PATIENTS SUFFERING FROM WASTING

CROSS REFERENCE TO RELATED APPLICATIONS

This application is the 371 National Phase of International Application No. PCT/CA2004/001843, filed Oct. 20, 2004, which was published in English under PCT Article 21(2) as International Publication No. WO 2005/037307. This application further claims the benefit, under 35 U.S.C. §119(e), of U.S. provisional patent application Ser. No. 60/512,198 filed Oct. 20, 2003. All of these applications are incorporated herein by reference in their entirety.

FIELD OF THE INVENTION

The invention relates to growth hormone (GH) secretagogues, such as GH releasing factor (GRF) and analogs thereof, and uses thereof.

BACKGROUND OF THE INVENTION

Wasting is a severe clinical condition associated with various diseases. Generally, this condition is characterized by a certain degree of involuntary weight loss, associated with a loss in lean body mass, whereas fat mass may decrease, increase or remain stable. In these patients, muscle wasting is very often associated with a poor prognosis and limited survival expectation, independently of the severity of the underlying disease.

An example of a wasting-type of condition is chronic obstructive pulmonary disease (COPD). COPD is characterized by progressive airflow obstruction due to chronic bronchitis or emphysema. Weight loss and muscle wasting are independent predictors of functional capacity and mortality in these patients (Schols et al. 1998). Consequently, anabolic interventions have been considered in order to promote muscle gain and muscle function. Nutritional repletion (Ferreira et al., 2000), anabolic steroids (Weisberg et al., 2002; Ferreira et al., 1998) as well as short term (3 weeks) administration of growth hormone (Burdet et al., 1997) have shown limited success particularly on muscle function. Although much attention is given to the pulmonary problems (emphysema, chronic bronchitis), it has become more and more a clinical reality in the past recent years that COPD is a multi-component disease, implying two major components, the pulmonary and the periphery (muscle mass). The evolution of these two components is not parallel. Several prospective and retrospective studies have clearly demonstrated that involuntary weight loss or a loss in lean body mass are independent predictors of mortality, and are associated with diminished endurance exercise capacity, impaired quality of life and increase utilization of health care costs.

Because of its anabolic effects and the decrease of its secretion in aging, growth hormone (GH) has been the subject of numerous clinical trials aiming at increasing muscle mass and functionality in several clinical conditions. Most of the clinical studies aiming at improving muscle mass and function in patients by a growth hormone replacement therapy have been conducted with recombinant human GH (rhGH), and resulted most frequently in increases in lean body mass, both in healthy volunteers and special patient populations. However, these changes in body composition have resulted in very inconsistent changes in muscle function, which is a desired clinical outcome. In that regard, Zachwieja et al. (1999) reviewed a series of studies done in healthy older volunteers, showing consistent increases in lean body mass, that were only rarely associated with increases in muscle strength. In COPD patients, two studies have been conducted with recombinant growth hormone. Both of them resulted in significant increases in lean body mass, but one of them (Pape et al., 1991) reported functional improvement, only in the form of an improved maximal inspiration pressure ($PI_{max}$), whereas the other (Burdet et al, 1997) failed to show any change in $PI_{max}$, handgrip strength or exercise capacity.

Another condition associated with wasting is HIV infection or AIDS. In these particular conditions, administration of recombinant GH has shown positive effects, both on body composition and on exercise performance (Schambelan et al., 1996).

Therefore, it appears from the scientific literature that GH replacement therapy in patients with various degrees of wasting most often results in important changes in body composition towards an increase in muscle mass, but in variable results in term of muscle functionality and clinical status. The variability in functional outcome of anabolic therapy is critical to the success of the therapy to the patient suffering from cachexia or wasting. There is thus a great need for therapeutics capable of restoring in wasting patients, not only muscle mass, but also muscle function.

SUMMARY OF THE INVENTION

The invention relates to GH secretagogues (e.g. GRF and analogs thereof) and uses thereof.

In a first aspect, the present invention provides a method of increasing muscle function in a subject, said method comprising administering to said subject an agent selected from the group consisting of (a) a growth hormone (GH) secretagogue and (b) a composition comprising a GH secretagogue and a pharmaceutically acceptable carrier. In an embodiment, the GH secretagogue is selected from the group consisting of GH-releasing factor (GRF) and a GRF analog. In another embodiment, the GRF analog is a GRF analog of formula A:

X-GRF Peptide                                                    (A)

wherein;

the GRF peptide is a peptide of formula B;

(SEQ ID NO: 1)
A1-A2-Asp-Ala-Ile-Phe-Thr-A8-Ser-Tyr-Arg-Lys-A13-

Leu-A15-Gln-Leu-A18-Ala-Arg-Lys-Leu-Leu-A24-A25-

Ile-A27-A28-Arg-A30-R0(B)

wherein,
   A1 is Tyr or His;
   A2 is Val or Ala;
   A8 is Asn or Ser;
   A13 is Val or Ile;
   A15 is Ala or Gly;
   A18 is Ser or Tyr;
   A24 is Gln or His;
   A25 is Asp or Glu;
   A27 is Met, Ile or Nle
   A28 is Ser or Asn;
   A30 is a bond or amino acid sequence of 1 up to 15 residues; and
   R0 is $NH_2$ or $NH-(CH_2)n-CONH_2$, with n=1 to 12; and
   X is a hydrophobic tail anchored via an amide bond to the N-terminus of the peptide and the hydrophobic tail defining a backbone of 5 to 7 atoms;

wherein the backbone can be substituted by $C_{1-6}$ alkyl, $C_{3-6}$ cycloalkyl, or $C_{6-12}$ aryl and the backbone comprises at least one rigidifying moiety connected to at least two atoms of the backbone;

said moiety selected from the group consisting of double bond, triple bond, saturated or unsaturated $C_{3-9}$ cycloalkyl, and $C_{6-12}$ aryl.

In a further embodiment, X is selected from the group consisting of:

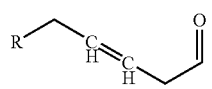

1

($R = H$ or $CH_3$ or $CH_2CH_3$)
cis or trans

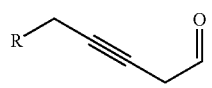

2

($R = H$ or $CH_3$ or $CH_2CH_3$)

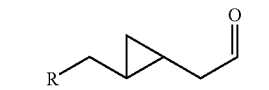

3

($R = H$ or $CH_3$ or $CH_2CH_3$)
cis or trans, both as racemic mixtures

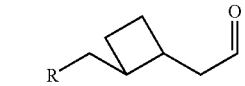

4

($R = H$ or $CH_3$ or $CH_2CH_3$)
cis or trans, both as racemic mixtures
or pure enantiomeric pairs

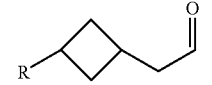

5

($R = H$ or $CH_3$ or $CH_2CH_3$)
cis or trans, (when $R \neq H$)

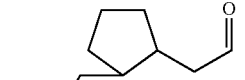

6

($R = H$ or $CH_3$ or $CH_2CH_3$)
cis or trans, both as racemic mixtures
or pure enantiomeric pairs

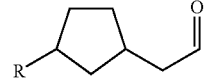

7

($R = H$ or $CH_3$ or $CH_2CH_3$)
cis or trans, (when $R \neq H$)
both as racemic mixtures
or pure enantiomeric pairs -continued

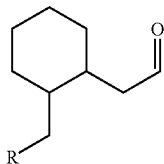

8

($R = H$ or $CH_3$ or $CH_2CH_3$)
cis or trans, both as racemic mixtures
or pure enantiomeric pairs

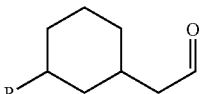

9

($R = H$ or $CH_3$ or $CH_2CH_3$)
cis or trans, (when $R \neq H$)
both as racemic mixtures
or pure enantiomeric pairs

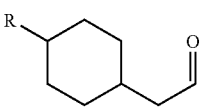

10

($R = H$ or $CH_3$ or $CH_2CH_3$)
cis or trans, (when $R \neq H$)

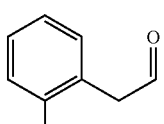

11

($R = H$ or $CH_3$ or $CH_2CH_3$)

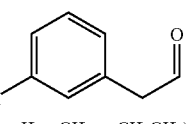

12

($R = H$ or $CH_3$ or $CH_2CH_3$)

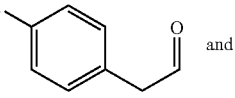

and

13

($R = H$ or $CH_3$ or $CH_2CH_3$)

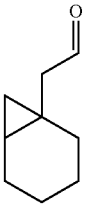

14

In yet another embodiment, A30 is selected from the group consisting of (a) a bond, (b) an amino acid sequence corresponding to positions 30-44 of a natural GRF peptide, and (c) the amino acid sequence of (b) having a 1-14 amino acid deletion from its C-terminus. In yet a further embodiment, the GRF peptide is selected from the group consisting of (a) a polypeptide comprising the amino acid sequence of SEQ ID NO: 3, (b) a polypeptide comprising the amino acid sequence of SEQ ID NO: 5; and (c) the polypeptide of (a) having a 1 to 14 amino acid deletion from its C-terminus. In embodiments, the GRF analog is (hexenoyl trans-3)hGRF(1-44)NH₂ (SEQ ID NO: 7).

In another aspect, the present invention also provides a method for increasing a muscle function wherein the muscle function is selected from the group consisting of (a) muscle strength, (b) muscle endurance and (c) both (a) and (b). In an embodiment, the muscle function is muscle strength, and in a further embodiment, the muscle strength is peripheral muscle strength. In another embodiment, the muscle function is muscle endurance. In a further embodiment, the increase in muscle function results in a reduction of a parameter selected from the group consisting of (a) breathing discomfort, (b) leg discomfort and (c) both (a) and (b). In yet a further embodiment, the increase results in an increase in lean body mass in the subject and/or a decrease in fat mass in the subject. In another embodiment, the subject suffers from wasting, and in a further embodiment, wasting is associated with a condition selected from the group consisting of chronic obstructive pulmonary disease, chronic renal failure, congestive hear failure, human immunodeficiency virus infection, acquired immunodeficiency syndrome, cancer, malnutrition, frailty, immobilization paraplegia and spinal disorder. In yet another embodiment, the subject suffers from severe wasting. In an embodiment, the subject has a body mass index less than or equal to 20 and/or a weight less than 90% of ideal body weight. In an embodiment, the subject is a male and has a fat free mass index less than or equal to 16 or the subject is a female and has a fat free mass index less than or equal to 15. In embodiments, the agent is administered in a route selected from the group consisting of intravenous, oral, transdermal, subcutaneous, mucosal, intramuscular, intranasal, intrapulmonary, parenteral, intrarectal and topical. In another embodiment, the GH secretagogue is administered in a dose from about 0.0001 mg to about 4 mg, in a further embodiment, from about 0.0001 to about 2 mg, in a further embodiment, from about 1 mg to about 2 mg, in a further embodiment, about 1 mg, in a further embodiment, about 2 mg.

In another aspect, the present invention provides use of an agent selected from the group consisting of (a) a growth hormone (GH) secretagogue and (b) a composition comprising a GH secretagogue and a pharmaceutically acceptable carrier; for increasing muscle function in a subject. In an embodiment, the GH secretagogue is selected from the group consisting of GH-releasing factor (GRF) and a GRF analog. In another embodiment, the GRF analog is a GRF analog of formula A:

X-GRF Peptide                                                (A)

wherein;

the GRF peptide is a peptide of formula B;

```
                                          (SEQ ID NO: 1)
A1-A2-Asp-Ala-Ile-Phe-Thr-A8-Ser-Tyr-Arg-Lys-A13-

Leu-A15-Gln-Leu-A18-Ala-Arg-Lys-Leu-Leu-A24-A25-

Ile-A27-A28-Arg-A30-R0 (B)
``` wherein,
  A1 is Tyr or His;
  A2 is Val or Ala;
  A8 is Asn or Ser;
  A13 is Val or Ile;
  A15 is Ala or Gly;
  A18 is Ser or Tyr;
  A24 is Gln or His;
  A25 is Asp or Glu;
  A27 is Met, Ile or Nle;
  A28 is Ser or Asn;
  A30 is a bond or amino acid sequence of 1 up to 15 residues; and R0 is NH₂ or NH—(CH2)n-CONH₂, with n=1 to 12; and X is a hydrophobic tail anchored via an amide bond to the N-terminus of the peptide and the hydrophobic tail defining a backbone of 5 to 7 atoms;

wherein the backbone can be substituted by $C_{1-6}$ alkyl, $C_{3-6}$ cycloalkyl, or $C_{6-12}$ aryl and the backbone comprises at least one rigidifying moiety connected to at least two atoms of the backbone;

said moiety selected from the group consisting of double bond, triple bond, saturated or unsaturated $C_{3-9}$ cycloalkyl, and $C_{6-12}$ aryl.

In yet another embodiment, X is selected from the group consisting of:

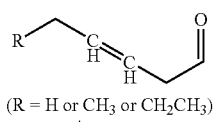

(R = H or CH₃ or CH₂CH₃)
cis or trans

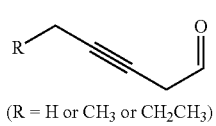

(R = H or CH₃ or CH₂CH₃)

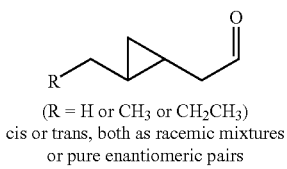

(R = H or CH₃ or CH₂CH₃)
cis or trans, both as racemic mixtures
or pure enantiomeric pairs

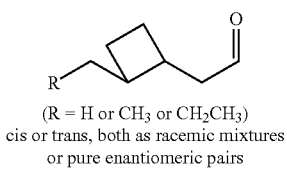

(R = H or CH₃ or CH₂CH₃)
cis or trans, both as racemic mixtures
or pure enantiomeric pairs

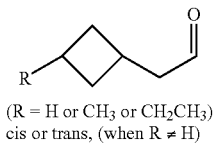

(R = H or CH₃ or CH₂CH₃)
cis or trans, (when R ≠ H)

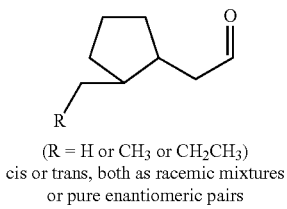

(R = H or CH₃ or CH₂CH₃)
cis or trans, both as racemic mixtures
or pure enantiomeric pairs -continued

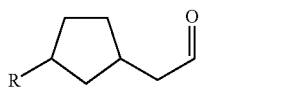

(R = H or CH₃ or CH₂CH₃)
cis or trans, (when R ≠ H)
both as racemic mixtures
or pure enantiomeric pairs

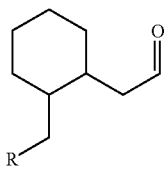

(R = H or CH₃ or CH₂CH₃)
cis or trans, both as racemic mixtures
or pure enantiomeric pairs

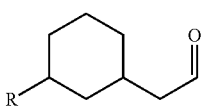

(R = H or CH₃ or CH₂CH₃)
cis or trans, (when R ≠ H)
both as racemic mixtures
or pure enantiomeric pairs

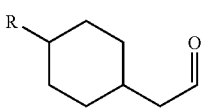

(R = H or CH₃ or CH₂CH₃)
cis or trans, (when R ≠ H)

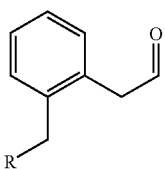

(R = H or CH₃ or CH₂CH₃)

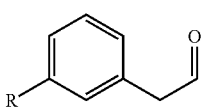

(R = H or CH₃ or CH₂CH₃)

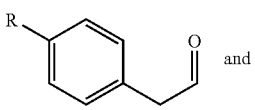

and (R = H or CH₃ or CH₂CH₃)

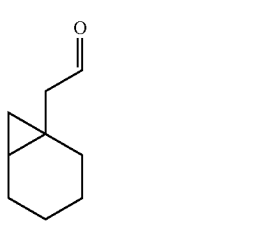

In yet a further embodiment, A30 is selected from the group consisting of (a) a bond, (b) an amino acid sequence corresponding to positions 30-44 of a natural GRF peptide, and (c) the amino acid sequence of (b) having a 1-14 amino acid deletion from its C-terminus. In yet another embodiment, the GRF peptide is selected from the group consisting of (a) a polypeptide comprising the amino acid sequence of SEQ ID NO: 3, (b) a polypeptide comprising the amino acid sequence of SEQ ID NO: 5 and (c) the polypeptide of (a) having a 1 to 14 amino acid deletion from its C-terminus. In embodiments, the GRF analog is (hexenoyl trans-3)hGRF(1-44)NH₂ (SEQ ID NO: 7).

In a further aspect, the invention also provides use of an agent for increasing a muscle function, wherein the muscle function is selected from the group consisting of (a) muscle strength, (b) muscle endurance; and (c) both (a) and (b). In an embodiment, the muscle function is muscle strength, and in a further embodiment, peripheral muscle strength. In another embodiment, the muscle function is muscle endurance. In yet another embodiment, the increase in muscle function results in a reduction of a parameter selected from the group consisting of (a) breathing discomfort, (b) leg discomfort and (c) both (a) and (b). In a further embodiment, the increase in muscle function results in an increase in lean body mass in the subject and/or a decrease in fat mass in the subject. In another embodiment, the subject suffers from wasting, and in a further embodiment, wasting is associated with a condition selected from the group consisting of chronic obstructive pulmonary disease, chronic renal failure, congestive hear failure, human immunodeficiency virus infection, acquired immunodeficiency syndrome, cancer, malnutrition, frailty, immobilization paraplegia and spinal disorder. In yet another embodiment, the subject suffers from severe wasting. In an embodiment, the subject may have a body mass index less than or equal to 20 and/or a weight less than 90% of ideal body weight. In an embodiment, the subject is a male and has a fat free mass index less than or equal to 16 or the subject is a female and has a fat free mass index less than or equal to 15. In another embodiment, the agent is adapted for an administration route selected from the group consisting of intravenous, oral, transdermal, subcutaneous, mucosal, intramuscular, intranasal, intrapulmonary, parenteral, intrarectal and topical. In a further embodiment, the GH secretagogue is adapted for administration in a dose from about 0.0001 mg to about 4 mg, in a further embodiment, from about 0.0001 to about 2 mg, in a further embodiment, from about 1 mg to about 2 mg, in a further embodiment, about 1 mg, in a further embodiment, about 2 mg.

In yet another aspect, the present invention provides use of an agent selected from the group consisting of (a) a growth hormone (GH) secretagogue and (b) a composition comprising a GH secretagogue and a pharmaceutically acceptable carrier; for the manufacture of a medicament for increasing muscle function in a subject.

In a further aspect, the present invention provides a package comprising (i) an agent selected from the group consisting of (a) a growth hormone (GH) secretagogue and (b) a composition comprising a GH secretagogue and a pharmaceutically acceptable carrier; and (ii) instructions for increasing muscle function in a subject. In an embodiment, the GH secretagogue is selected from the group consisting of GH-releasing factor (GRF) and a GRF analog. In another embodiment, the GRF analog is a GRF analog of formula A:

X-GRF Peptide (A)

wherein;

the GRF peptide is a peptide of formula B;

```
                                              (SEQ ID NO: 1)
A1-A2-Asp-Ala-Ile-Phe-Thr-A8-Ser-Tyr-Arg-Lys-A13-

Leu-A15-Gln-Leu-A18-Ala-Arg-Lys-Leu-Leu-A24-A25-

Ile-A27-A28-Arg-A30-R0(B)
``` wherein,
A1 is Tyr or His;
A2 is Val or Ala;
A8 is Asn or Ser;
-A13 is Val or Ile;
A15 is Ala or Gly;
A18 is Ser or Tyr;
A24 is Gln or His;
A25 is Asp or Glu;
A27 is Met, Ile or Nle
A28 is Ser or Asn;
A30 is a bond or amino acid sequence of 1 up to 15 residues; and R0 is NH$_2$ or NH—(CH$_2$)n-CONH$_2$, with n=1 to 12; and X is a hydrophobic tail anchored via an amide bond to the N-terminus of the peptide and the hydrophobic tail defining a backbone of 5 to 7 atoms;

wherein the backbone can be substituted by $C_{1-6}$ alkyl, $C_{3-6}$ cycloalkyl, or $C_{6-12}$ aryl and the backbone comprises at least one rigidifying moiety connected to at least two atoms of the backbone;

said moiety selected from the group consisting of double bond, triple bond, saturated or unsaturated $C_{3-9}$ cycloalkyl, and $C_{6-12}$ aryl.

In yet another embodiment, X is selected from the group consisting of:

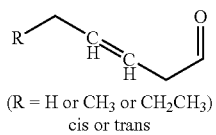

1

(R = H or CH$_3$ or CH$_2$CH$_3$)
cis or trans

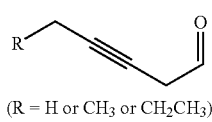

2

(R = H or CH$_3$ or CH$_2$CH$_3$)

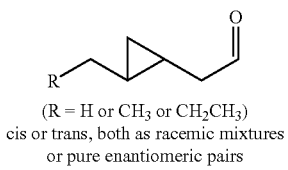

3

(R = H or CH$_3$ or CH$_2$CH$_3$)
cis or trans, both as racemic mixtures
or pure enantiomeric pairs

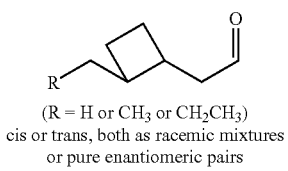

4

(R = H or CH$_3$ or CH$_2$CH$_3$)
cis or trans, both as racemic mixtures
or pure enantiomeric pairs -continued

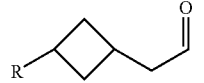

5

(R = H or CH$_3$ or CH$_2$CH$_3$)
cis or trans, (when R ≠ H)

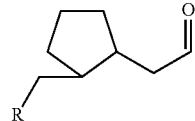

6

(R = H or CH$_3$ or CH$_2$CH$_3$)
cis or trans, both as racemic mixtures
or pure enantiomeric pairs

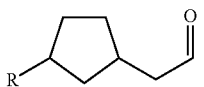

7

(R = H or CH$_3$ or CH$_2$CH$_3$)
cis or trans, (when R ≠ H)
both as racemic mixtures
or pure enantiomeric pairs

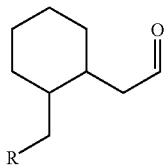

8

(R = H or CH$_3$ or CH$_2$CH$_3$)
cis or trans, both as racemic mixtures
or pure enantiomeric pairs

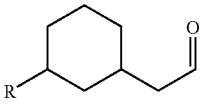

9

(R = H or CH$_3$ or CH$_2$CH$_3$)
cis or trans, (when R ≠ H)
both as racemic mixtures
or pure enantiomeric pairs

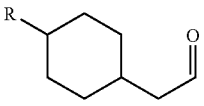

10

(R = H or CH$_3$ or CH$_2$CH$_3$)
cis or trans, (when R ≠ H)

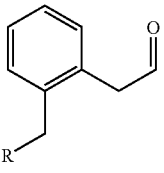

11

(R = H or CH$_3$ or CH$_2$CH$_3$)

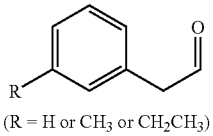

12

(R = H or CH$_3$ or CH$_2$CH$_3$)

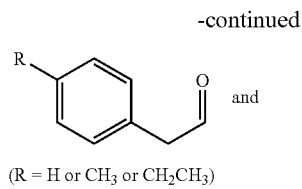

(R = H or CH₃ or CH₂CH₃)

In yet a further embodiment, A30 is selected from the group consisting of (a) a bond, (b) an amino acid sequence corresponding to positions 30-44 of a natural GRF peptide, and (c) the amino acid sequence of (b) having a 1-14 amino acid deletion from its C-terminus. In yet a further embodiment, the GRF peptide is selected from the group consisting of (a) a polypeptide comprising the amino acid sequence of SEQ ID NO: 3, (b) a polypeptide comprising the amino acid sequence of SEQ ID NO: 5; and (c) the polypeptide of (a) having a 1 to 14 amino acid deletion from its C-terminus. In another embodiment, the GRF analog is (hexenoyl trans-3) hGRF(1-44)NH₂ (SEQ ID NO: 7).

In another aspect, the invention provides a package comprising instructions for increasing muscle function. In an embodiment, the muscle function is selected from the group consisting of (a) muscle strength, (b) muscle endurance and (c) both (a) and (b). In an embodiment, the muscle function is muscle strength, and in a further embodiment, peripheral muscle strength. In another embodiment, the muscle function is muscle endurance. In yet another embodiment, said increase in muscle function results in a reduction of a parameter selected from the group consisting of (a) breathing discomfort, (b) leg discomfort, and (c) both (a) and (b). In another embodiment, the increase in muscle function results in an increase in lean body mass in the subject and/or a decrease in fat mass in said subject. In a further embodiment, the subject suffers from wasting, and in a further embodiment, wasting is associated with a condition selected from the group consisting of chronic obstructive pulmonary disease (COPD), chronic renal failure, congestive hear failure, human immunodeficiency virus infection, acquired immunodeficiency syndrome, cancer, malnutrition, frailty, immobilization paraplegia and spinal disorder. In another embodiment, the subject suffers from severe wasting. In an embodiment, the subject has a body mass index less than or equal to 20 and/or a weight less than 90% of ideal body weight. In an embodiment, the subject is a male and has fat free mass index less than or equal to 16 or the subject is a female and has a fat free mass index less than or equal to 15. In another embodiment, the agent is adapted for an administration route selected from the group consisting of intravenous, oral, transdermal, subcutaneous, mucosal, intramuscular, intranasal, intrapulmonary, parenteral, intrarectal and topical. In yet another embodiment, the GH secretagogue is adapted for administration in a dose between about 0.0001 mg to about 4 mg, in a further embodiment, from about 0.0001 to about 2 mg, in a further embodiment, from about 1 mg to about 2 mg, in a further embodiment, about 1 mg, in a further embodiment, about 2 mg.

In yet a further aspect, the present invention provides a composition for increasing muscle function in a subject, the composition comprising (a) a growth hormone (GH) secretagogue and (b) a pharmaceutically acceptable carrier. In an embodiment, the GH secretagogue is selected from the group consisting of a GH-releasing factor (GRF) and a GRF analog. In a further embodiment, the GRF analog is a GRF analog of formula A:

X-GRF Peptide            (A)

wherein;

the GRF peptide is a peptide of formula B;

```
                                           (SEQ ID NO: 1)
A1-A2-Asp-Ala-Ile-Phe-Thr-A8-Ser-Tyr-Arg-Lys-A13-

Leu-A15-Gln-Leu-A18-Ala-Arg-Lys-Leu-Leu-A24-A25-

Ile-A27-A28-Arg-A30-R0(B)
``` wherein,

A1 is Tyr or His;

A2 is Val or Ala;

A8 is Asn or Ser;

A13 is Val or Ile;

A15 is Ala or Gly;

A18 is Ser or Tyr;

A24 is Gln or His;

A25 is Asp or Glu;

A27 is Met, Ile or Nle

A28 is Ser or Asn;

A30 is a bond or amino acid sequence of 1 up to 15 residues; and

R0 is NH₂ or NH—(CH₂)n-CONH₂, with n=1 to 12; and

X is a hydrophobic tail anchored via an amide bond to the N-terminus of the peptide and the hydrophobic tail defining a backbone of 5 to 7 atoms;

wherein the backbone can be substituted by $C_{1-6}$ alkyl, $C_{3-6}$ cycloalkyl, or $C_{6-12}$ aryl and the backbone comprises at least one rigidifying moiety connected to at least two atoms of the backbone;

said moiety selected from the group consisting of double bond, triple bond, saturated or unsaturated cycloalkyl, and $C_{6-12}$ aryl.

In another embodiment, X is selected from the group consisting of:

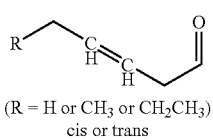

(R = H or CH₃ or CH₂CH₃)
cis or trans

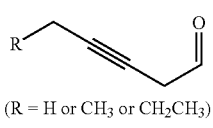

(R = H or CH₃ or CH₂CH₃)

-continued

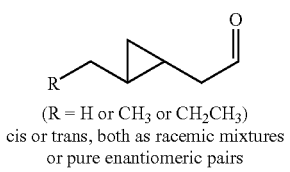

(R = H or CH₃ or CH₂CH₃)
cis or trans, both as racemic mixtures
or pure enantiomeric pairs

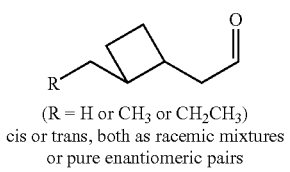

(R = H or CH₃ or CH₂CH₃)
cis or trans, both as racemic mixtures
or pure enantiomeric pairs

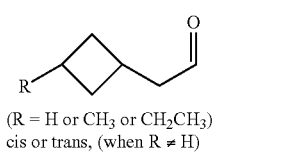

(R = H or CH₃ or CH₂CH₃)
cis or trans, (when R ≠ H)

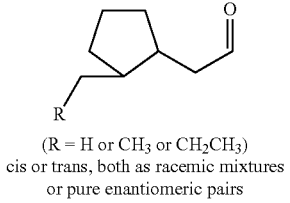

(R = H or CH₃ or CH₂CH₃)
cis or trans, both as racemic mixtures
or pure enantiomeric pairs

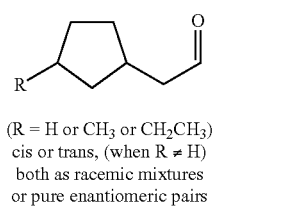

(R = H or CH₃ or CH₂CH₃)
cis or trans, (when R ≠ H)
both as racemic mixtures
or pure enantiomeric pairs

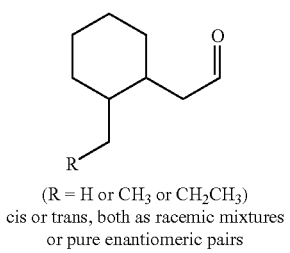

(R = H or CH₃ or CH₂CH₃)
cis or trans, both as racemic mixtures
or pure enantiomeric pairs

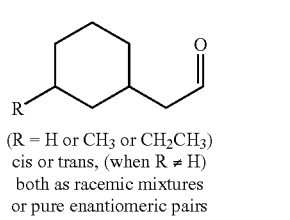

(R = H or CH₃ or CH₂CH₃)
cis or trans, (when R ≠ H)
both as racemic mixtures
or pure enantiomeric pairs

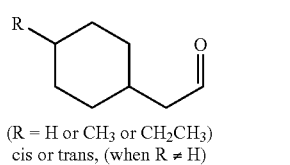

(R = H or CH₃ or CH₂CH₃)
cis or trans, (when R ≠ H)

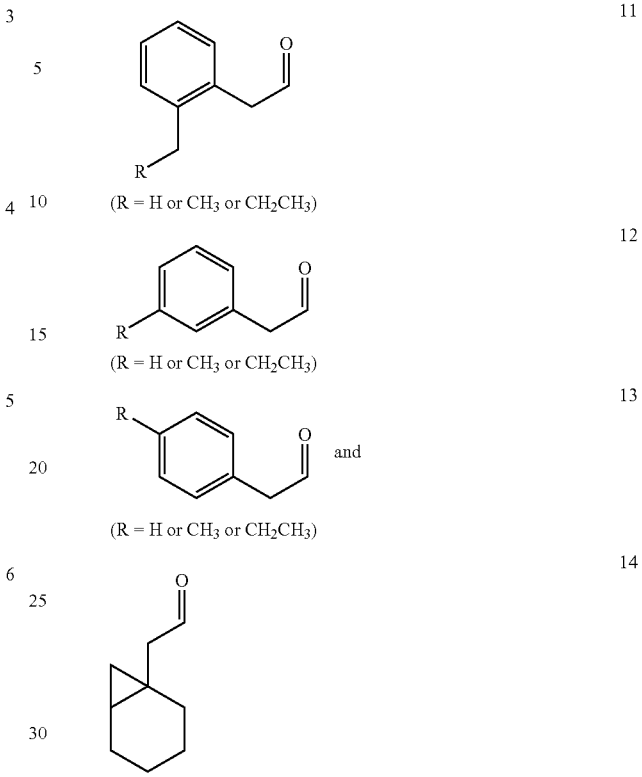

In a further embodiment, A30 is selected from the group consisting of (a) a bond, (b) an amino acid sequence corresponding to positions 30-44 of a natural GRF peptide, and (c) the amino acid sequence of (b) having a 1-14 amino acid deletion from its C-terminus. In yet another embodiment, the GRF peptide is selected from the group consisting of (a) a polypeptide comprising the amino acid sequence of SEQ ID NO: 3, (b) a polypeptide comprising the amino acid sequence of SEQ ID NO: 5; and (c) the polypeptide of (a) having a 1 to 14 amino acid deletion from its C-terminus. In a further embodiment, the GRF analog is (hexenoyl trans-3)hGRF(1-44)NH₂ (SEQ ID NO: 7).

DETAILED DESCRIPTION OF THE INVENTION

Figure 1:
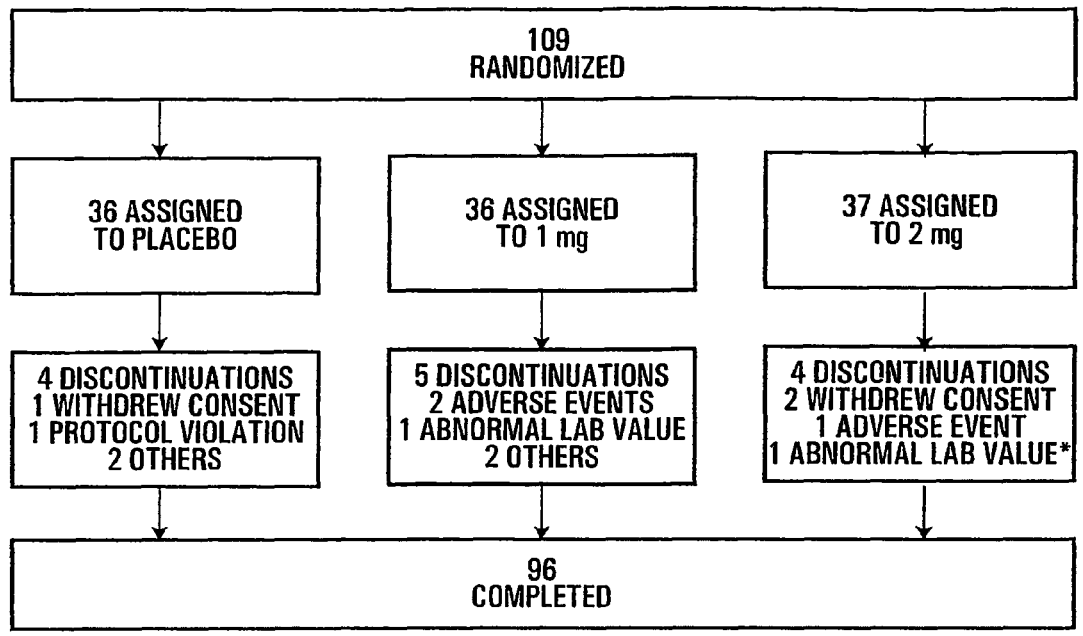
FIG. 1. Disposition of Subjects of the study presented herein.

This invention relates to a new use of a GH secretagogue, more specifically to a new use of GRF or its analogs. This invention also relates to a method for improving muscle function.

In a first aspect, this invention provides a method of increasing muscle function in a subject. In an embodiment, the method comprises administering an agent selected from the group consisting of a growth hormone (GH) secretagogue and a composition comprising a GH secretagogue and a pharmaceutically acceptable carrier. "GH secretagogue" as used herein refers to any compound or molecule, natural or synthetic, which may result in, either directly or indirectly, GH secretion and/or an increase in GH secretion.

In embodiments, the GH secretagogue is a growth hormone-releasing factor (GRF; also referred to as growth hormone releasing hormone [GHRH]) or a GRF analog.

In an embodiment, the GRF is human GRF (hGRF).

Human growth hormone-releasing factor (hGRF) is a peptide of 44 amino acids with a C-terminal $NH_2$ modification, referred to herein as hGRF(1-44)$NH_2$, and has the following structure:

(SEQ ID NO: 2)
Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser-Arg-Gln-Gln-Gly-Glu-Ser-Asn-Gln-

Glu-Arg-Gly-Ala-Arg-Ala-Arg-Leu-$NH_2$

Therefore, the amino acid sequence of the just-noted 44 amino acid form is as follows:

(SEQ ID NO: 3)
Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser-Arg-Gln-Gln-Gly-Glu-Ser-Asn-Gln-

Glu-Arg-Gly-Ala-Arg-Ala-Arg-Leu

The minimum active core comprises the first 29 amino acids of the above sequence, which is referred to herein as hGRF(1-29)$NH_2$, and has the following structure:

(SEQ ID NO: 4)
Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser-Arg-$NH_2$

Therefore, the amino acid sequence of the just-noted 29 amino acid form is as follows:

(SEQ ID NO: 5)
Tyr-Ala-Asp-Ala-Ile-Phe-Thr-Asn-Ser-Tyr-Arg-Lys-

Val-Leu-Gly-Gln-Leu-Ser-Ala-Arg-Lys-Leu-Leu-Gln-

Asp-Ile-Met-Ser-Arg

The 1-44 and 1-29 forms differ in that the 1-44 form contains the following additional amino acids, which correspond to positions 30-44 of the 1-44 form:

(SEQ ID NO: 6)
Gln-Gln-Gly-Glu-Ser-Asn-Gln-Glu-Arg-Gly-Ala-Arg-

Ala-Arg-Leu

In an embodiment, the GRF analog is a GRF analog of formula A:

X-GRF Peptide          (A)

wherein;
the GRF peptide is a peptide of formula B;

(B) (SEQ ID NO: 1)
A1-A2-Asp-Ala-Ile-Phe-Thr-A8-Ser-Tyr-Arg-Lys-A13-

Leu-A15-Gln-Leu-A18-Ala-Arg-Lys-Leu-Leu-A24-A25-

Ile-A27-A28-Arg-A30-R0 wherein,
A1 is Tyr or His;
A2 is Val or Ala;
A8 is Asn or Ser;
A13 is Val or Ile;
A15 is Ala or Gly;
A18 is Ser or Tyr;
A24 is Gln or His;
A25 is Asp or Glu;
A27 is Met, Ile or Nle
A28 is Ser or Asn;
A30 is a bond or amino acid sequence of 1 up to 15 residues; and
R0 is $NH_2$ or NH—$(CH_2)n$-$CONH_2$, with n=1 to 12; and
X is a hydrophobic tail anchored via an amide bond to the N-terminus of the peptide and the hydrophobic tail defining a backbone of 5 to 7 atoms;
wherein the backbone can be substituted by $C_{1-6}$ alkyl, $C_{3-6}$ cycloalkyl, or $C_{6-12}$ aryl and the backbone comprises at least one rigidifying moiety connected to at least two atoms of the backbone;
said moiety selected from the group consisting of double bond, triple bond, saturated or unsaturated $C_{3-9}$ cycloalkyl, and $C_{6-12}$ aryl.

In embodiments, X noted above is selected from the group consisting of:

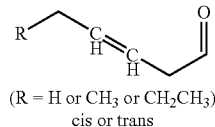

(R = H or $CH_3$ or $CH_2CH_3$)
cis or trans

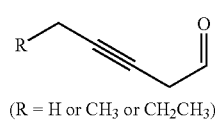

(R = H or $CH_3$ or $CH_2CH_3$)

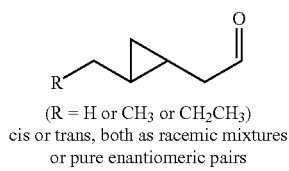

(R = H or $CH_3$ or $CH_2CH_3$)
cis or trans, both as racemic mixtures
or pure enantiomeric pairs -continued

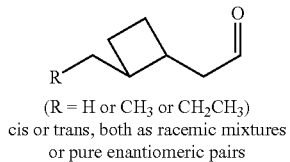
(R = H or CH₃ or CH₂CH₃)
cis or trans, both as racemic mixtures
or pure enantiomeric pairs

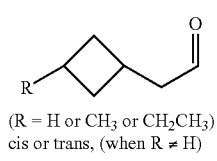
(R = H or CH₃ or CH₂CH₃)
cis or trans, (when R ≠ H)

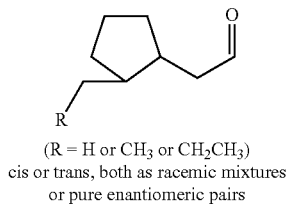
(R = H or CH₃ or CH₂CH₃)
cis or trans, both as racemic mixtures
or pure enantiomeric pairs

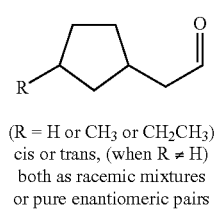
(R = H or CH₃ or CH₂CH₃)
cis or trans, (when R ≠ H)
both as racemic mixtures
or pure enantiomeric pairs

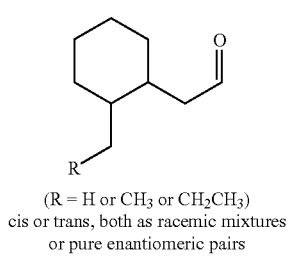
(R = H or CH₃ or CH₂CH₃)
cis or trans, both as racemic mixtures
or pure enantiomeric pairs

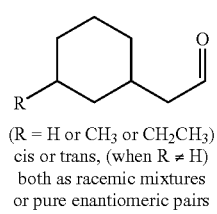
(R = H or CH₃ or CH₂CH₃)
cis or trans, (when R ≠ H)
both as racemic mixtures
or pure enantiomeric pairs

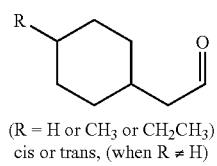
(R = H or CH₃ or CH₂CH₃)
cis or trans, (when R ≠ H)

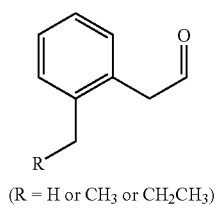
(R = H or CH₃ or CH₂CH₃)

-continued

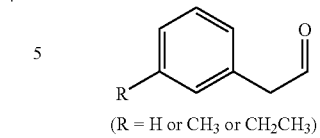
(R = H or CH₃ or CH₂CH₃)

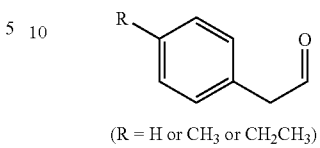
(R = H or CH₃ or CH₂CH₃)

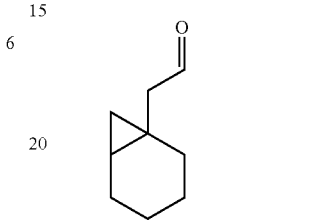

In embodiments, A30 noted above is selected from the group consisting of a bond, an amino acid sequence corresponding to positions 30-44 of a natural GRF peptide and said an amino acid sequence from the 30-44 fragment having a 1-14 amino acid deletion from its C-terminus.

In embodiments, the above-noted GRF peptide is selected from the group consisting of a polypeptide comprising the amino acid sequence of SEQ ID NO: 3; a polypeptide comprising the amino acid sequence of SEQ ID NO: 5; and the polypeptide of (a) having a 1 to 14 amino acid deletion from its C-terminus.

In an embodiment, the above-noted GRF analog is (hexenoyl trans-3)hGRF(1-44)NH₂.

Methods of preparing the above-described GRF analogs are described in U.S. Pat. No. 5,861,379 (Ibea et al., Jan. 19, 1999); U.S. Pat. No. 6,020,311 (Brazeau et al., Feb. 1, 2000), U.S. Pat. No. 6,458,764 (Gravel et al., Oct. 1, 2002) and published US application No. 2004/0171534 A1 (Gravel et al., published Sep. 2, 2004).

In embodiments, the invention also provides methods of treating a mammal, and further, a human.

In embodiments, the methods described herein also relate to improving muscle function. "Muscle function", as used herein, is defined as the action for which a muscle is specially adapted, specialized or used. For example, pulmonary muscles, such as the diaphragm, are used to contract and expand the lungs to enable expiration and inspiration. As such, an increase in pulmonary muscle function would result in increased breathing abilities, such as an increase in pulmonary inspiratory pressure ($PI_{max}$). The determination of muscle function is specific to each muscle. Techniques for determining muscle function, such as the $PI_{max}$, are generally to known to those skilled in the art (refer to examples below).

The methods described herein relates to improving muscle strength. As used herein "muscle strength" is defined as the power to resist a force. Muscle strength can be measured by various techniques known to those skilled in the art (refer to the examples below) ("Skeletal Muscle Dysfunction in Chronic Obstructive Pulmonary Disease", American Thoracic Society and European Respiratory Society Statement, AM J Respir Crit. Care Med Vol 159, pp S1-S400, 1999). In an embodiment, muscle strength is peripheral muscle strength (e.g. quadriceps strength).

In another embodiment, the methods described herein relate to improving muscle endurance. As used herein, "muscle endurance" is defined as the ability to sustain a prolonged stressful effort or activity. Techniques for determining muscle endurance are specific to each muscle and are generally known to those skilled in the art (refer to the examples below). For an example of determination of muscle endurance, refer to "Measurement of Symptoms, Lung Hyperinflation, and Endurance during Exercise in Chronic Obstructive Pulmonary Disease", Denis E. O'Donnell, Miu Lam, and Katherine A. Webb, Am J. Respir Crit. Care Med 1998; 158:1557-1565.

In embodiments, the methods described herein result in a decrease in breathing discomfort and/or leg discomfort (or leg fatigue).

In further embodiments, the methods result in an increase in lean body mass and/or a decrease in fat mass. Lean body mass refers the weight of the subject in the absence of fat. It thus includes the weight of bones, organs, muscles, etc. The fat mass is thus the remainder of the weight of the subject. The lean body weight can be estimated using the following formulas:

For men=$(1.10 \times \text{Weight(kg)}) - 128 \times (\text{Weight}^2/(100 \times \text{Height(m)})^2)$ For women=$(1.07 \times \text{Weight(kg)}) - 148 \times (\text{Weight}^2/(100 \times \text{Height(m)})^2)$ The lean body mass (and ultimately fat mass) can also be assessed quantitatively using dual X-ray absorptiometry (or DEXA) (Morabia et al., 1999).

In embodiments, the methods concern subjects who may be suffering from wasting. Wasting is a condition associated with a reduction in size of an organ or tissue. It is usually associated with lean mass loss, and more specifically muscle mass loss. It is also referred to as "cachexia" or "muscle depletion". Wasting may be associated with several conditions such as chronic obstructive pulmonary disease, chronic renal failure, congestive heart failure, HIV infection, AIDS, cancer, malnutrition, frailty (e.g. associated with aging), immobilization (e.g. due to a stroke), paraplegia, spinal disorders, etc. In a further embodiment, the subjects may be suffering from severe wasting (e.g. severe muscle depletion or severe cachexia). As used herein, "severe wasting" is associated with an excessive loss of muscle mass. This excessive loss of muscle mass can be observed typically in patients suffering from one or more listed above.

There are several well-recognized ways to define the body composition and, ultimately, the degree of muscle wasting or muscle depletion in subjects. In an embodiment, the degree of muscle depletion is measured by the involuntary weight loss over a defined period of time. In another embodiment, body composition is calculated as a percentage of ideal body weight (IBW). The IBW is defined as the ratio of the patient's weight over an ideal weight for his gender, age and height based on the "Metropolitan Life" tables. In a further embodiment, the body composition of a subject can be calculated by using Body Mass Index (BMI). The BMI is calculated using the following formula:

$$BMI = \frac{\text{Weight (in kg)}}{\text{Height}^2 \text{ (in meters)}}$$

Subjects having a BMI between 20 and 25 are considered to have a normal body weight. Subjects having a BMI lower than 20 are considered to have severe muscle depletion or to be suffering from wasting. Subjects having a BMI higher than 25 are considered overweight, and higher than 30, obese. In another embodiment, body composition is measure quantitatively by the dual energy x-ray absorptiometry (DEXA) technique ("Dual-energy x-ray absorptiometry for total-body and regional bone-mineral and soft-tissue composition" Richard B. Mazess, Howard S. Barden, Joseph P. Bisek and James Hanson. Am J Clin Nutr 1990; 51:1106-12). This technique allows the determination of lean body mass, or fat-free-mass (sum of lean body mass and bone mineral mass) and the fat mass (total weight–fat-free mass). DEXA also allows the determination of the lean body mass index (LBMI) and the fat free mass index (FFMI) ("Physiologic Effects of Nutritional Support and Anabolic Steroids in Patients with Chronic Obstructive Pulmonary Disease"—Annemie M. W. J. Schols, Peter B. Soeters, Rob Mostert, Rob J. Pluymers, and Emiel F. M. Wouters, A M J. Respir. Crit. Care Med 1995; 152:1268-74.).

It is generally reported in the art that patients are considered to have a severe wasting if their body mass index (BMI) is less than or equal to 20, or if their weight is less than or equal to 90% of ideal body weight, or if their fat free mass index (FFMI) is less than or equal to 16 (in men) or 15 (in women). These values can vary from one clinical condition to another.

As noted above, in various embodiments, the above-mentioned GH secretagogue may be used therapeutically in formulations or medicaments to effect the above-noted increase in muscle function and to prevent or treat the above-noted conditions. The invention provides corresponding methods of medical treatment, in which a therapeutic dose of a GH secretagogue is administered in a pharmacologically acceptable formulation, e.g. to a patient or subject in need thereof. Accordingly, the invention also provides therapeutic compositions comprising a GH secretagogue and a pharmacologically acceptable excipient or carrier. In one embodiment, such compositions include a GH secretagogue in a therapeutically or prophylactically effective amount sufficient to effect the above-noted increase in muscle function and to treat the above-noted conditions. The therapeutic composition may be soluble in an aqueous solution at a physiologically acceptable pH.

A "therapeutically effective amount" refers to an amount effective, at dosages and for periods of time necessary, to achieve the desired therapeutic result, such as to effect the above-noted increase in muscle function and to reduce the progression of the above-noted conditions. A therapeutically effective amount of a GH secretagogue may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as preventing or inhibiting the rate of onset or progression of the above-noted conditions. A prophylactically effective amount can be determined as described above for the therapeutically effective amount. For any particular subject, specific dosage regimens may be adjusted over time according to the individual need and the professional judgement of the person administering or supervising the administration of the compositions. In an embodiment, the GH secretagogue dosage is from about 0.0001 mg to about 4 mg, in a further embodiment, from about 0.0001 to about 2 mg, in a further embodiment, from about 1 mg to about 2 mg, in a further embodiment, about 1 mg, in a further embodiment, about 2 mg.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, subcutaneous, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, a GH secretagogue can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g. a GH secretagogue in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, a GH secretagogue may be formulated with one or more additional compounds that enhance its solubility.

In accordance with another aspect of the invention, therapeutic compositions of the present invention, comprising a GH secretagogue, may be provided in containers, kits or packages (e.g. commercial packages) which further comprise instructions for its use to effect the above-noted increase in muscle function and to prevent or treat the above-noted conditions. The instructions may indicate that the uses result in a decrease in breathing discomfort and/or leg discomfort, a decrease in fat mass or an increase in lean body mass.

Accordingly, the invention further provides a package (e.g. commercial package) comprising a GH secretagogue or the above-mentioned composition together with instructions to effect the above-noted increase in muscle function and to prevent or treat the above-noted conditions.

The invention further provides use of a GH secretagogue to effect the above-noted increase in muscle function and to prevent or treat the above-noted conditions. The invention further provides use of a GH secretagogue for the preparation of a medicament to effect the above-noted increase in muscle function and to prevent or treat the above-noted conditions. The administration of the composition of the present invention can be from a route selected from the group consisting of oral, transdermal, intravenous, subcutaneous, mucosal, intramuscular, intranasal, intrapulmonary, parenteral, intrarectal and topical route. In embodiments, the above-noted instructions may indicate that the agent or composition may be administered subcutaneously. In further embodiments, the instructions may also indicate that the GH secretagogue dosage is administered in a dose from about 0.0001 mg to about 4 mg, in a further embodiment, from about 0.0001 to about 2 mg, in a further embodiment, from about 1 mg to about 2 mg, in a further embodiment, about 1 mg, in a further embodiment, about 2 mg.

In another aspect, the invention also provides compositions comprising a GH secretagogue and a pharmaceutically acceptable carrier. In an embodiment, the composition can be used for improving muscle function, muscle strength and/or muscle endurance.

The results presented herein clearly show that administration of a GH secretagogue (such as the GRF analogue, TH9507), to patients suffering from wasting (e.g. COPD-associated wasting) significantly increased serum IGF-1 levels, augmented lean body mass, decreased fat mass and, surprisingly, improved muscle strength, muscle function and muscle endurance.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Study Drug

The compound used in the studies below is (hexenoyl trans-3)hGRF(1-44)NH$_2$ (also referred to as TH9507 herein), which is a synthetic human growth hormone releasing factor analog that comprises the 44-amino acid sequence of human growth hormone releasing factor (hGRF) on which a hexenoyl moiety, a $C_6$ side chain has been anchored on Tyr 1 at the $NH_2$-terminal. (hexenoyl trans-3)hGRF(1-44)$NH_2$ or TH9507 has the following structure:

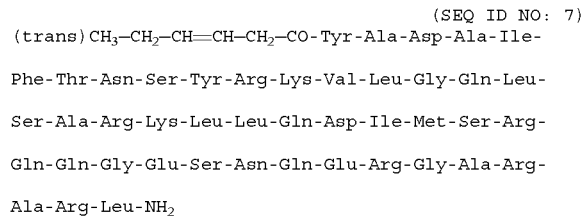

(hexenoyl trans-3)hGRF(1-44)$NH_2$ was synthesized via the methods set forth in U.S. Pat. No. 5,861,379 (Ibea et al.; Jan. 19, 1999).

Example 2

Material and Methods

The results presented herein were obtained from a multi-centre, randomized, double-blind, placebo-controlled study. The compound TH9507 was administered by subcutaneous injection daily (1 or 2 mg dose) for a three-month period. Patients were of both genders, aged 50 years or older, with stable COPD as per the 1995 American Thoracic Society criteria.

Body Mass Index (BMI) criteria. For subjects aged between 50 and 64, their BMI was less than or equal to 27 (kg/m$^2$). For these subjects, if their BMI was between 23 and 27, their forced expiratory volume in one second (FEV1) is less than or equal to 50% of predicted value (Hankinson J L, Odencrantz J R, Fedan K P. Spirometric reference values from a sample of the general US population. AM J. Respir Crit. Care Med. 1999; 159:179-187). For subjects aged 65 or older, their BMI was less than or equal to 28 (kg/m$^2$). For these subjects, if their BMI was between 24 and 28, their forced expiratory volume in one second (FEV1) is less than or equal to 50% of predicted value (Hankinson J L, Odencrantz J R, Fedan K P. Spirometric reference values from a sample of the general US population. AM J. Respir Crit Care Med. 1999; 159:179-187).

Statistics. ANOVA was used to compare the changes from baseline at Month 1, 2 and 3. It also includes comparisons between groups using Tukey adjustments. Repeated Measures Analyses were used to assess overall treatment effect (inter-group analyses) and overall time effect (within group analyses).

Population analyzed. Population were analyzed using ITT-LOCF (Intent To Treat-Last Observation Carried Forward). Subgroups have been created according to the following criteria: low Fat Free Mass Index (Low FFMI <15 for women, <16 for men), low BMI (BMI <20).

Example 3

Disposition of Subjects

Adverse events and safety laboratory parameters (haematology, biochemistry, urinalysis) were measured using standard laboratory methods.

The disposition of subjects of the study presented herein are shown in FIG. 1. The number of premature discontinuation was comparable in the 3 groups. None of the reasons for discontinuation was related to study drug except for one patient in the 2 mg group who showed elevated creatine phosphokinase (CPK) and serum glutamic oxaloacetic transaminase (SGOT) values (*) following 1 month of treatment and that were considered to be possibly related to treatment.

Table 1 (below) presents the baseline characteristics of the subjects of the study.

TABLE 1

| Baseline Characteristics. Data are presented as means ± SD. | | | |
|---|---|---|---|
| | Placebo | 1 mg | 2 mg |
| N | 36 | 36 | 37 |
| Women | 8 | 7 | 7 |
| Men | 28 | 29 | 30 |
| Age (years) | 65.5 ± 8.6 | 64.7 ± 7.6 | 63.4 ± 8.4 |
| (Min-Max) | (46.3-80.6) | (48.9-84.7) | (49.6-79.5) |
| BMI (kg/m$^2$) | 21.9 ± 2.9 | 21.8 ± 3.4 | 22.5 ± 3.5 |
| FEV1% pred. | 40.7 ± 12.8 | 35.2 ± 13.2 | 37.7 ± 12.7 |
| (Min-Max) | (22.2-66.8) | (15.9-63.6) | (12.4-63.2) |
| Median | 37.9 | 35.0 | 37.6 |
| IGF-1 (ng/mL) | 115 ± 39 | 115 ± 44 | 112 ± 34 |

Example 4

Serum IGF-1 Levels Over the Study Period

Serum IGF-1 were measured after acid-ethanol extraction using the Esoterix™ RIA kit (Esoterix Inc., Calabasas Hill, Calif.) according to the manufacturer's instructions. The sensitivity of this kit is 10 ng/mL.

Figure 2:
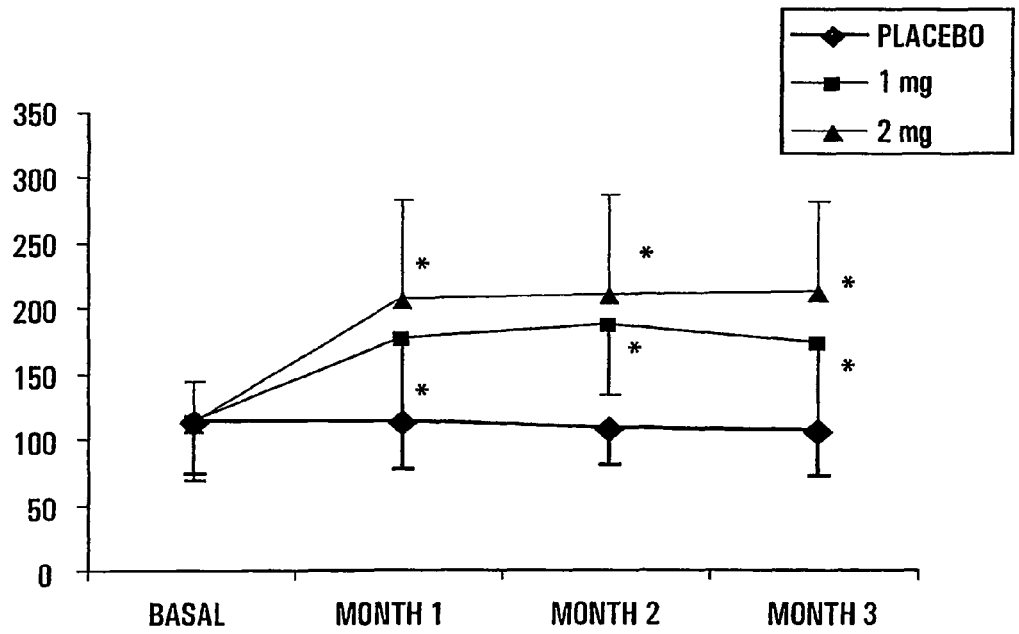
FIG. 2. Serum IGF-1 levels over the study period. Data are presented as means±standard deviation (SD).

A significant increase over baseline was observed at each study time point in both TH9507-treated groups (*P<0.001, FIG. 2) with the following changes at Month 3: placebo: −6%; 1 mg: +50%; 2 mg: +92%. Treatment effect was dose-related (P<0.001) and significantly different when compared to placebo (P<0.001) (FIG. 2.). Similarly, significant increase in IGF-1 as compared to baseline and placebo were observed in the low FFMI and low BMI populations (+103% and +129% at Month 3, respectively).

Example 5

Change in Body Composition

Body composition (lean body mass and fat mass) were assessed by Dual-Energy X-Ray Absorptiometry (DEXA).

Figure 3A:
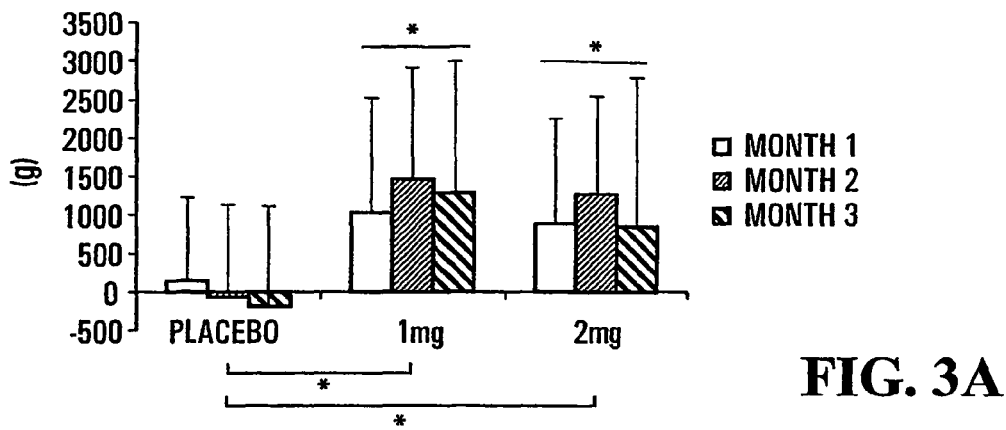
FIG. 3. Changes in Lean Body Mass in the overall (A), low FFMI (B) and low BMI (C) populations. Data are presented as means±SD.
Figure 3B:
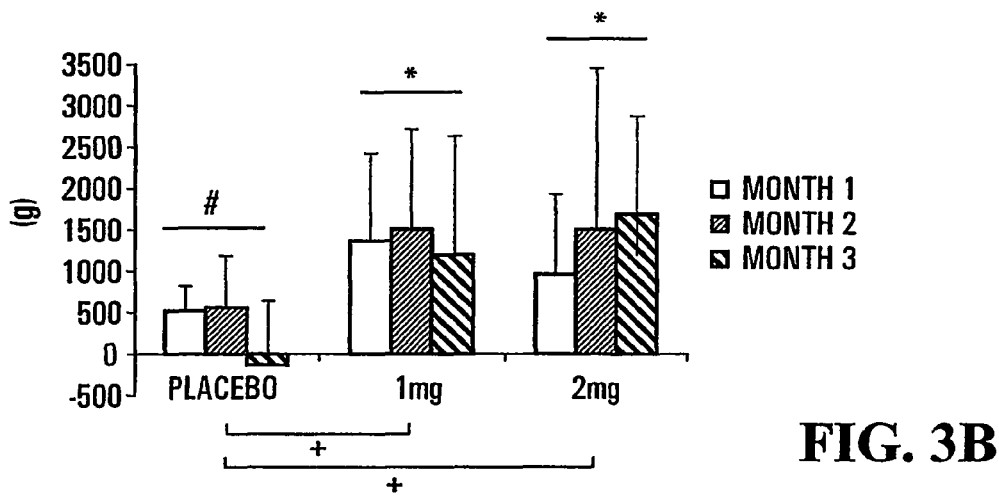
Figure 3C:
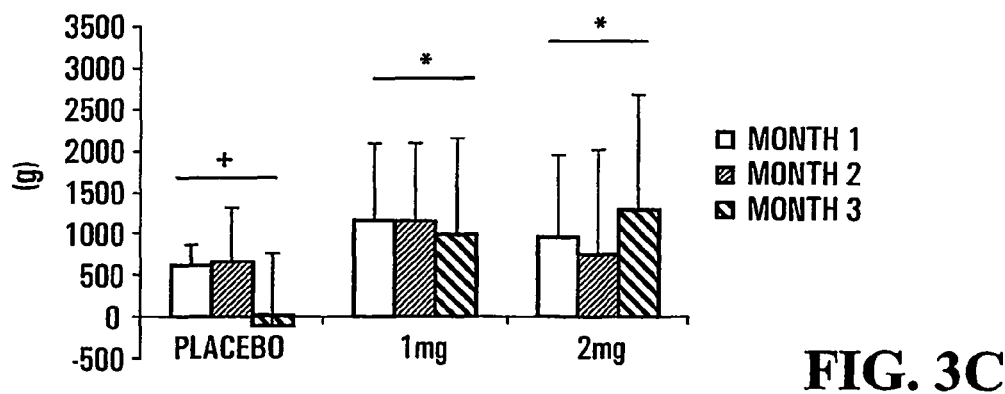

Lean body mass. In the overall population, lean body mass significantly increased at both doses when compared to baseline and to placebo (*P<0.001, FIG. 3A). Gains were noticeable as early as Month 1. At Month 3, changes were as follows: placebo: −0.1 kg; 1 mg: +1.3 kg, 2 mg: +0.9 kg. For the low FFMI population, lean body mass significantly increased at both doses when compared to baseline (*P<0.001) and to placebo (P<0.05)(FIG. 3B). At the end of the treatment period, changes were as follows: placebo: −0.1 kg; 1 mg: +1.2 kg; 2 mg: +1.7 kg. For the low BMI population, lean body mass increased at both doses when compared to baseline (*P<0.001) (FIG. 3C). At the end of the treatment period, changes were as follows: placebo: −0.1 kg; 1 mg: +1 kg; 2 mg: +1.3 kg.

Figure 4:
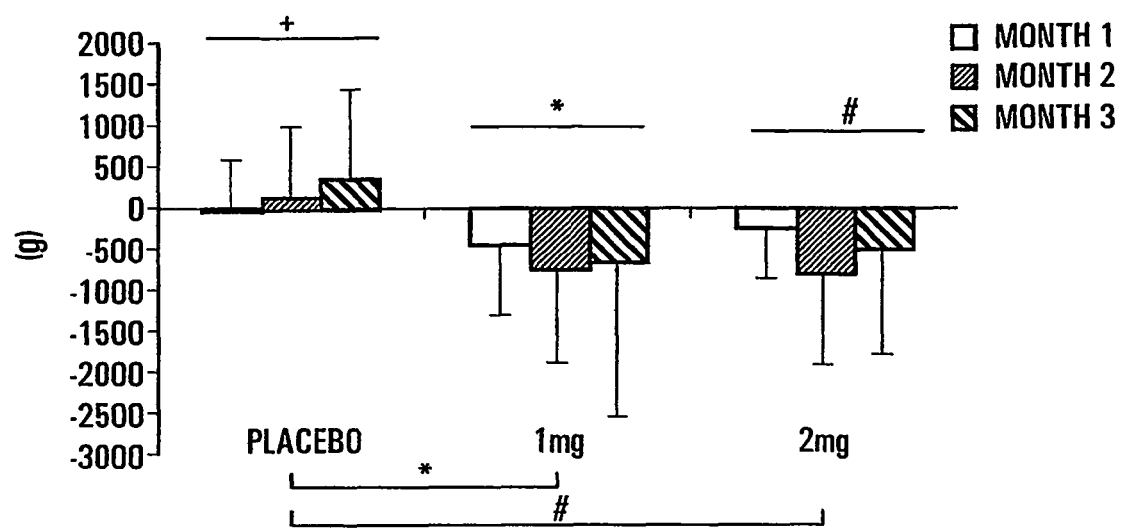
FIG. 4. Changes in Fat Mass in the overall population. Data are presented as means±SD.

Fat mass. For the overall population, fat mass significantly decreased at both doses when compared to baseline (*P<0.001, #P<0.01) whereas an increase was observed in the placebo group (+P<0.05)(FIG. 4). Changes were significant when compared to placebo but not between the treated groups. At the end of the treatment period, changes were as follows: placebo: +0.4 kg; 1 mg: −0.7 kg; 2 mg: −0.5 kg. Similarly, significant decreases in fat mass as compared to baseline and placebo were observed in the low FFMI (placebo: +0.1 kg; 1 mg: −1.1 kg; 2 mg: −0.9 kg—at Month 3) and low BMI populations (placebo: +0.4 kg; 1 mg: −1.0 kg; 2 mg: −1.1 kg at Month 3).

Example 6

Muscle Function

Peripheral muscle strength was measured by isokinetic muscle strength testing. Briefly, in order to assess the quadriceps muscle strength, the subjects must extend their knee at 90°/sec.

During an exercise performed with a cycle ergometer at 75% of maximal capacity, Borg scale at isotime for evaluation of dyspnea and leg discomfort were measured.

Figure 5A:
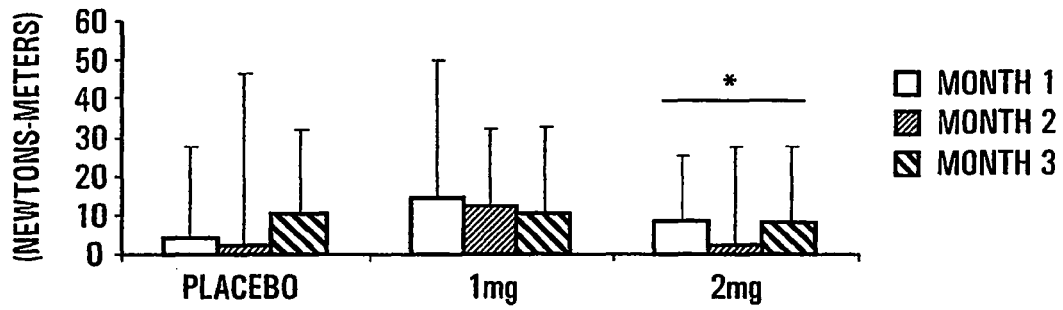
FIG. 5. Changes over baseline in muscle strength (knee extension at 90°/sec.) in the overall (A), low FFMI (B) and low BMI (C) populations. Data are presented as means±SD.
Figure 5B:
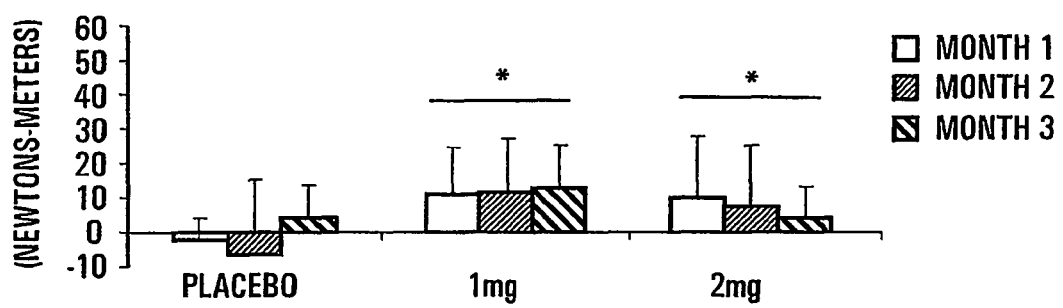
Figure 5C:
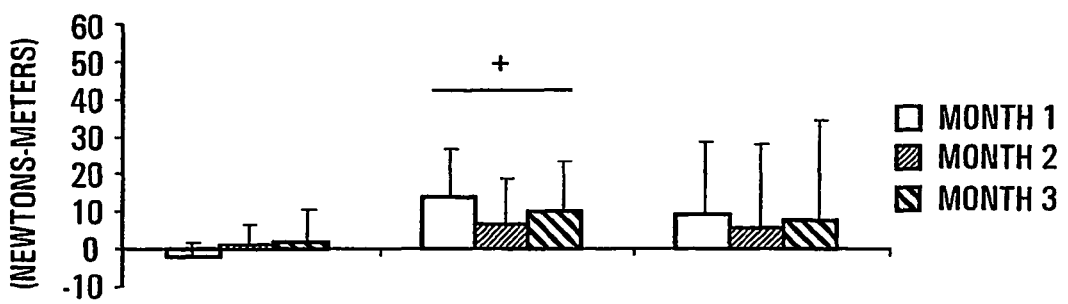

Muscle strength. For the overall population, muscle strength significantly increased over baseline at 2 mg (*$P<0.05$) (FIG. 5A). For the 1 mg dose, a trend was observed ($P=0.06$) (FIG. 5A). For the low FFMI population, significant results over baseline were observed within both TH9507-treated groups (*$P<0.05$) (FIG. 5B). For the low BMI population, muscle strength was significantly increased over baseline at 1 mg (+$P<0.01$) while a trend was observed at 2 mg ($P=0.08$) (FIG. 5C). Table 2 presents individual muscle strength results.

TABLE 2

Summary of individual changes in muscle strength (knee extension at 90°/sec). Data are percentage of subject with changes in muscle strength ≧10% vs. baseline.

| | Month 1 increase | Month 2 increase | Month 3 increase |
|---|---|---|---|
| Total Population | | | |
| Placebo | 18.8% | 28.1% | 34.4% |
| 1 mg | 38.7% | 38.7% | 45.2% |
| 2 mg | 46.9% | 37.5% | 40.6% |

TABLE 2-continued

Summary of individual changes in muscle strength (knee extension at 90°/sec). Data are percentage of subject with changes in muscle strength ≧10% vs. baseline.

| | Month 1 increase | Month 2 increase | Month 3 increase |
|---|---|---|---|
| Low BMI | | | |
| Placebo | 0.0% | 0.0% | 25.0% |
| 1 mg | 57.1% | 57.1% | 57.1% |
| 2 mg | 44.4% | 55.6% | 55.6% |
| Low FFMI | | | |
| Placebo | 0.0% | 0.0% | 30.0% |
| 1 mg | 40.0% | 70.0% | 70.0% |
| 2 mg | 44.4% | 55.6% | 44.4% |

Figure 6A:
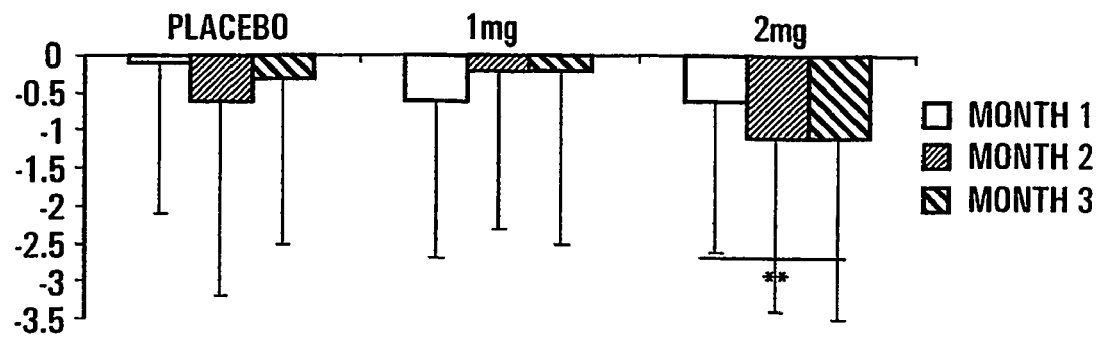
FIG. 6. Changes in Borg Scale for Breathing (A) and Leg (B) discomfort during the cycle ergometer test. Data are presented as means±SD.
Figure 6B:
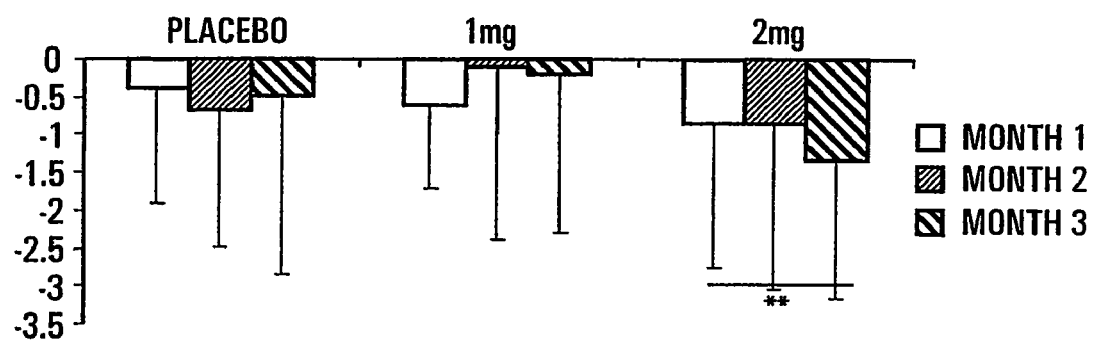

Both breathing and leg discomfort (or leg fatigue) Borg scales are significantly decreased over baseline at the 2 mg dose indicating an improvement in both symptoms (**$P<0.01$) (FIGS. 6A and B).

Throughout this application, various references are referred to describe more fully the state of the art to which this invention pertains. The disclosures of these references are hereby incorporated by reference into the present disclosure.

REFERENCES

Zachwieja et al. Phys Ther. 1999; 79(1): 76-82.
Pape et al. Chest. 1991; 99(6): 1495-1500.
Burdet et al. Am J Respir Crit. Care Med. 1997; 156(6):1800-1806.
Schambelan et al. Ann Intern Med. 1996; 125: 873-882.
A M Schols et al. Am J Respir Crit. Care Med. 1998; 157: 1791-1797.
I Martins Ferreira et al. Chest. 2000; 117:672-678.
Weisberg J et al. Chest. 2002; 121: 1070-1078.
I Martins Ferreira et al. Chest. 1998; 114: 19-28.
L Burdet et al. Am J Respir Crit. Care Med. 1997; 156: 1800-1806.
Morabia et al. Br J Nutr. 1999; 82(1): 49-55.

What is claimed is:

1. A method of increasing muscle function in a subject suffering from severe wasting, said method comprising administering to said subject the GRF analog (hexenoyl trans-3)hGRF(1-44)NH$_2$ (SEQ ID NO: 7), wherein said subject has at least one of the following characteristics:
   (a) said subject has a body mass index less than or equal to 20;
   (b) said subject has a weight less than 90% of ideal body weight;
   (c) said subject is a male and said subject has a fat free mass index less than or equal to 16; or
   (d) said subject is a female and said subject has a fat free mass index less than or equal to 15.

2. The method of claim 1, wherein said muscle function is selected from the group consisting of:
   (a) muscle strength;
   (b) muscle endurance; and
   (c) both (a) and (b).

3. The method of claim 2, wherein said muscle function is muscle strength.

4. The method of claim 3, wherein said muscle strength is peripheral muscle strength.

5. The method of claim 2, wherein said muscle function is muscle endurance.

6. The method of claim 1, wherein said administering reduces a parameter selected from the group consisting of:
(a) breathing discomfort;
(b) leg discomfort; and
(c) both (a) and (b).

7. The method of claim 1, wherein said administering increases lean body mass in said subject.

8. The method of claim 1, wherein said administering decreases fat mass in said subject.

9. The method of claim 1, wherein said wasting is associated with a condition selected from the group consisting of chronic obstructive pulmonary disease, chronic renal failure, congestive hear failure, human immunodeficiency virus infection, acquired immunodeficiency syndrome, cancer, malnutrition, frailty, immobilization paraplegia and spinal disorder.

10. The method of claim 1, wherein said GRF analog is administered through a route selected from the group consisting of intravenous, oral, transdermal, subcutaneous, mucosal, intramuscular, intranasal, intrapulmonary, parenteral, intrarectal and topical.

11. The method of claim 1, wherein said GRF analog is administered in a dose from about 0.0001 mg to about 4 mg.

12. The method of claim 11, wherein said GRF analog is administered in a dose selected from the group consisting of about 1 mg and about 2 mg.

* * * * *

UNITED STATES PATENT AND TRADEMARK OFFICE
CERTIFICATE OF CORRECTION

PATENT NO. : 7,893,025 B2  Page 1 of 1
APPLICATION NO. : 10/576439
DATED : February 22, 2011
INVENTOR(S) : Lussier et al.

It is certified that error appears in the above-identified patent and that said Letters Patent is hereby corrected as shown below:

Front page, (73) Assignee: "Theratechnolgies Inc." should read
--Theratechnologies Inc.--

Signed and Sealed this
Eleventh Day of September, 2012

David J. Kappos
*Director of the United States Patent and Trademark Office*

SEQUENCE LISTING

```
<160> NUMBER OF SEQ ID NOS: 7

<210> SEQ ID NO 1
<211> LENGTH: 44
<212> TYPE: PRT
<213> ORGANISM: Artificial sequence
<220> FEATURE:
<223> OTHER INFORMATION: GRF peptide
<220> FEATURE:
<221> NAME/KEY: VARIANT
<222> LOCATION: (1)..(1)
<223> OTHER INFORMATION: Xaa = Tyr or His
<220> FEATURE:
<221> NAME/KEY: VARIANT
<222> LOCATION: (2)..(2)
<223> OTHER INFORMATION: Xaa = Val or Ala
<220> FEATURE:
<221> NAME/KEY: VARIANT
<222> LOCATION: (8)..(8)
<223> OTHER INFORMATION: Xaa = Asn or Ser
<220> FEATURE:
<221> NAME/KEY: VARIANT
```

-continued

```
<222> LOCATION: (13)..(13)
<223> OTHER INFORMATION: Xaa = Val or Ile
<220> FEATURE:
<221> NAME/KEY: VARIANT
<222> LOCATION: (15)..(15)
<223> OTHER INFORMATION: Xaa = Ala or Gly
<220> FEATURE:
<221> NAME/KEY: VARIANT
<222> LOCATION: (18)..(18)
<223> OTHER INFORMATION: Xaa = Ser or Tyr
<220> FEATURE:
<221> NAME/KEY: VARIANT
<222> LOCATION: (24)..(24)
<223> OTHER INFORMATION: Xaa = Gln or His
<220> FEATURE:
<221> NAME/KEY: VARIANT
<222> LOCATION: (25)..(25)
<223> OTHER INFORMATION: Xaa = Asp or Glu
<220> FEATURE:
<221> NAME/KEY: VARIANT
<222> LOCATION: (27)..(27)
<223> OTHER INFORMATION: Xaa = Met or Ile or Nle
<220> FEATURE:
<221> NAME/KEY: VARIANT
<222> LOCATION: (28)..(28)
<223> OTHER INFORMATION: Xaa = Ser or Asn
<220> FEATURE:
<221> NAME/KEY: VARIANT
<222> LOCATION: (30)..(30)
<223> OTHER INFORMATION: Xaa = any amino acid or is absent
<220> FEATURE:
<221> NAME/KEY: VARIANT
<222> LOCATION: (31)..(31)
<223> OTHER INFORMATION: Xaa = any amino acid or is absent
<220> FEATURE:
<221> NAME/KEY: VARIANT
<222> LOCATION: (32)..(32)
<223> OTHER INFORMATION: Xaa = any amino acid or is absent
<220> FEATURE:
<221> NAME/KEY: VARIANT
<222> LOCATION: (33)..(33)
<223> OTHER INFORMATION: Xaa = any amino acid or is absent
<220> FEATURE:
<221> NAME/KEY: VARIANT
<222> LOCATION: (34)..(34)
<223> OTHER INFORMATION: Xaa = any amino acid or is absent
<220> FEATURE:
<221> NAME/KEY: VARIANT
<222> LOCATION: (35)..(35)
<223> OTHER INFORMATION: Xaa = any amino acid or is absent
<220> FEATURE:
<221> NAME/KEY: VARIANT
<222> LOCATION: (36)..(36)
<223> OTHER INFORMATION: Xaa = any amino acid or is absent
<220> FEATURE:
<221> NAME/KEY: VARIANT
<222> LOCATION: (37)..(37)
<223> OTHER INFORMATION: Xaa = any amino acid or is absent
<220> FEATURE:
<221> NAME/KEY: VARIANT
<222> LOCATION: (38)..(38)
<223> OTHER INFORMATION: Xaa = any amino acid or is absent
<220> FEATURE:
<221> NAME/KEY: VARIANT
<222> LOCATION: (39)..(39)
<223> OTHER INFORMATION: Xaa = any amino acid or is absent
<220> FEATURE:
<221> NAME/KEY: VARIANT
<222> LOCATION: (40)..(40)
<223> OTHER INFORMATION: Xaa = any amino acid or is absent
<220> FEATURE:
<221> NAME/KEY: VARIANT
<222> LOCATION: (41)..(41)
<223> OTHER INFORMATION: Xaa = any amino acid or is absent
<220> FEATURE:
<221> NAME/KEY: VARIANT
<222> LOCATION: (42)..(42)
<223> OTHER INFORMATION: Xaa = any amino acid or is absent
<220> FEATURE:
```

```
<221> NAME/KEY: VARIANT
<222> LOCATION: (43)..(43)
<223> OTHER INFORMATION: Xaa = any amino acid or is absent
<220> FEATURE:
<221> NAME/KEY: VARIANT
<222> LOCATION: (44)..(44)
<223> OTHER INFORMATION: Xaa = any amino acid or is absent
<220> FEATURE:
<221> NAME/KEY: MOD_RES
<222> LOCATION: (44)..(44)
<223> OTHER INFORMATION: C-terminal residue is modified with NH2 or
      NH-(CH2)n-CONH2, with n=1 to 12

<400> SEQUENCE: 1

Xaa Xaa Asp Ala Ile Phe Tyr Xaa Ser Tyr Arg Lys Xaa Leu Xaa Gln
1               5                   10                  15

Leu Xaa Ala Arg Lys Leu Leu Xaa Xaa Ile Xaa Xaa Arg Xaa Xaa Xaa
            20                  25                  30

Xaa Xaa Xaa Xaa Xaa Xaa Xaa Xaa Xaa Xaa Xaa Xaa
        35                  40

<210> SEQ ID NO 2
<211> LENGTH: 44
<212> TYPE: PRT
<213> ORGANISM: Homo sapiens
<220> FEATURE:
<221> NAME/KEY: MISC_FEATURE
<222> LOCATION: (44)..(44)
<223> OTHER INFORMATION: Leu residue is capped with an unsubstituted
      amide moiety

<400> SEQUENCE: 2

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 3
<211> LENGTH: 44
<212> TYPE: PRT
<213> ORGANISM: Artificial sequence
<220> FEATURE:
<223> OTHER INFORMATION: Amino acid sequence of human GRF

<400> SEQUENCE: 3

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 4
<211> LENGTH: 29
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Arg residue is capped with an unsubstituted
      amide moiety

<400> SEQUENCE: 4

Tyr Ala Asp Ala Ile Phe Thr Asn Ser Tyr Arg Lys Val Leu Gly Gln
```

```
                                -continued
1               5              10             15

Leu Ser Ala Arg Lys Leu Leu Gln Asp Ile Met Ser Arg
            20                  25

<210> SEQ ID NO 5
<211> LENGTH: 29
<212> TYPE: PRT
<213> ORGANISM: Artificial sequence
<220> FEATURE:
<223> OTHER INFORMATION: Amino acid sequence of minimum active core of
      human GRF

<400> SEQUENCE: 5

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 6
<211> LENGTH: 15
<212> TYPE: PRT
<213> ORGANISM: Artificial sequence
<220> FEATURE:
<223> OTHER INFORMATION: Amino acid sequence corresponding to positions
      30 to 44 of human GRF

<400> SEQUENCE: 6

Gln Gln Gly Glu Ser Asn Gln Glu Arg Gly Ala Arg Ala Arg Leu
1               5                   10                  15

<210> SEQ ID NO 7
<211> LENGTH: 44
<212> TYPE: PRT
<213> ORGANISM: Artificial sequence
<220> FEATURE:
<223> OTHER INFORMATION: Modified GRF peptide
<220> FEATURE:
<221> NAME/KEY: MISC_FEATURE
<222> LOCATION: (1)..(1)
<223> OTHER INFORMATION: Tyr residue is linked to an hexenoyl-trans-3
      moiety
<220> FEATURE:
<221> NAME/KEY: MISC_FEATURE
<222> LOCATION: (44)..(44)
<223> OTHER INFORMATION: Leu residue is capped with an unsubstituted
      amide moiety

<400> SEQUENCE: 7

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40
```